US006255493B1

(12) United States Patent
Zhang

(10) Patent No.: US 6,255,493 B1
(45) Date of Patent: Jul. 3, 2001

(54) TRANSITION METAL-CATALYZED REACTIONS BASED ON CHIRAL AMINE OXAZOLINYL LIGANDS

(75) Inventor: Xumu Zhang, State College, PA (US)

(73) Assignee: The Penn State Research Foundation, Univserity Park, PA (US)

( * ) Notice: Subject to any disclaimer, the term of this patent is extended or adjusted under 35 U.S.C. 154(b) by 0 days.

(21) Appl. No.: 09/189,867

(22) Filed: Nov. 12, 1998

Related U.S. Application Data

(60) Provisional application No. 60/065,502, filed on Nov. 12, 1997.

(51) Int. Cl.$^7$ ............................ C07D 263/28; B01J 31/02
(52) U.S. Cl. ............................................. 548/238; 502/152
(58) Field of Search ............................................. 548/238

(56) References Cited

U.S. PATENT DOCUMENTS

| 3,192,224 | * | 6/1965 | Kapar ................................... 548/238 |
| 3,872,096 | * | 3/1975 | Witte et al. ........................... 548/238 |
| 3,979,405 | * | 9/1976 | Toth et al. ........................ 548/238 X |
| 4,497,812 | * | 2/1985 | Creuzet et al. ....................... 514/211 |

FOREIGN PATENT DOCUMENTS

0780157 A1    6/1997  (EP) .

OTHER PUBLICATIONS

Noyori, R. & Hashiguchi, S., "Asymmetric Transfer Hydrogenation Catalyzed by Chiral Ruthenium Complexes," *Acc. Chem. Res.*, 30, 97–102 (1997).

Haack, K.–J. et al., "The Catalyst Precursor, Catalyst, and Intermediate in the Ru$^{II}$–Promoted Asymmetric Hydrogen Transfer between Alcohols and Ketones," *Angew. Chem. Int. Ed. Engl.*, 36, No. 3 (1997).

Gamez, P. et al., "Asymmetric Catalytic Reduction of Carbonyl Compounds Using $C_2$ Symmetric Diamines as Chiral Ligands," *Tetrahedron: Asymmetry*, vol. 6, No. 3, 705–718 (1995).

Nishiyama, H. et al., "New Chiral Ruthenium Bix(oxazolinyl)pyridine Catalyst. Efficient Asymmetric Cyclopropanation of Olefins with Diazoacetates," *J. Am. Chem. Soc.*, 116, 2223–2224 (1994).

Nishiyama, H. et al., "Chiral Ruthenium(II)–Bis(2–oxazolin–2yl)pyridine Complexes. Asymmetric Catalytic Cyclopropanation of Olefins and Diazoacetates," *Bull. Chem. Soc. Jpn.*, 68, 1247–1262 (1995).

Evans, D. et al., "$C_2$ –Symmetric Cationic Copper(II) Complexes as Chiral Lewis Acids: Counterion Effects in the Enantioselective Diels–Alder Reaction," *Angew. Chem. Int. Ed. Engl.*, 34, No. 7 (1995).

Evans, D. et al., "$C_2$ –Symmetric Copper(II) Complexes as Chiral Lewis Acids. Catalytic Enantioselective Aldol Additions of Silylketene Acetals to (Benzyloxy)acetaldehyde," *J. Am. Chem. Soc.*, 118, 5814–5815 (1996).

Dox, A.W., "Acetamidine Hydrochloride," *Organic Syntheses*, vol. 1, 5–7 (1932).

Zassinovich, G. et al., "Asymmetric Hydrogen Transfer Reactions Promoted by Homogeneous Transition Metal Catalysts," *Chem. Rev.*, 92, 1051–1069 (1992).

de Graauw, C.F. et al., "Meerwein–Pondorf–Verley Reductions and Oppenauer Oxidations: An Integrated Approach," *Journal of Synthetic Organic Chemistry*, No. 10, 1007–1016 (1994).

Jiang, Y. et al., "Highly Effective NPN–type Tridentate Ligands for Asymmetric Transfer Hydrogenation of Ketones," *Tetrahedron Letters*, vol. 38, No. 2, 215–218 (1997).

Jiang, Y. et al., "New Chiral Ligands for Catalytic Asymmetric Transfer Hydrogenation of Ketones," *Tetrahedron Letters*, vol. 38, No. 37, 6565–6568 (1997).

Jiang, Q. et al., "Synthesis of (1R, 1R')–2,6–Bis[1–(diphenylphosphino)ethyl]pyridine and its Application in Asymmetric Transfer Hydrogenation," *Tetrahedron Letters*, vol. 37, No. 6, 797–800 (1996).

Sammakia, T. & Strangeland, E., "Transfer Hydrogenation with Ruthenium Complexes of Chiral (Phosphinoferrocenyl)oxazolines," *J. Org. Chem.*, 62, 6104–6105 (1997).

Evans, D. et al., "A Chiral Samarium–Based Catalyst for the Asymmetric Meerwein–Ponndorf–Verley Reduction," *J. Am. Chem. Soc.*, 115, 9800–9801 (1993).

Müller, D. et al., "21.$C_2$ –Symmetric 4,4',5,5'–Tetrahydrobi)oxazoles) and 4,4',5,5'–Tetrahydro–2,2'–methylenebis [oxazoles ]as Chiral Ligands for Enantioselective Catalysis," *Helvetica Chimica Acta*, vol. 74, 232–239 (1991).

Langer, T. & Helmchen, G., "Highly Efficient New Catalysts for Enantioselective Transfer Hydrogenation of Ketones," *Tetrahedron Letters*, vol. 37, No. 9, 1381–1384 (1996).

Gao, J–X., et al., "A Ruthenium(II) Complex with a $C_2$–Symmetric Diphosphine/Diamine Tetradentate Ligand for Asymmetric Transfer Hydrogenation of Aromatic Ketones," *Organometallics*, 15, 1087–1089 (1996).

Nishiyama, H., et al., Chiral and $C_2$–Symmetric Bis(oxazolinylpyridine)rhodium(III) Complexes: Effective Catalysts for Asymmetric Hydrosilylation of Ketones, *Organometallics*, 8, 846–848 (1989).

(List continued on next page.)

Primary Examiner—Floyd D. Higel
(74) Attorney, Agent, or Firm—Finnegan, Henderson, Farabow, Garrett & Dunner, L.L.P.

(57) ABSTRACT

The invention is drawn to transition metal catalysts for the practical synthesis of important chiral molecules. The transition metal catalysts comprise chiral ligands based on chiral amine oxazolinyl ligands. The invention includes methods of making the catalysts, and methods of performing reactions using the catalysts.

5 Claims, 4 Drawing Sheets

OTHER PUBLICATIONS

Nishiyama, H., et al., Highly Enantioselective Hydrosilylation of Ketones with Chiral and $C_2$–Symmetrical Bis(oxazolinyl)pyridine–Rhodium Catalysts, *Organometallics*, 10, 500–508 (1991).

Corey, E.J., et al., "Designed Catalyst for Enantioselective Diels–Alder Addition from a $C_2$–Symmetric Chiral Bis(oxazoline)–Fe(III) Complex," J. Am. Chem. Soc., 113, pp. 728–729 (1991).

Jiang, Yutong, et al., "A New Chiral Bis(oxazolinylmethyl)amine Ligand for Ru–Catalized from a Asymmetric Transfer Hydrogenation of Ketones," J. Am. Chem. Soc., 120, pp. 3817–3818 (1998).

Ghosh, Arun K., et al., "$C_2$–Symmetric Chiral Bis(oxazoline)–Metal Complexes in Catalytic Asymmetric Synthesis," Tetrahedron: Asymmetry vol. 9, pp. 1–45 (1998).

* cited by examinern=1,2

TRANSITION METAL-CATALYZED REACTIONS BASED ON CHIRAL AMINE OXAZOLINYL LIGANDS

CROSS REFERENCE TO RELATED APPLICATIONS

This application claims priority to U.S. provisional application No. 60/065,502, filed Nov. 12, 1997, incorporated by reference in its entirety. Government funding was provided by the Office of Naval Research, ONR No. N00014-96-1-0733.

Government funding by the Office of Naval Research, ONR=N00014-96-0733, was utilized during development of this invention.

BACKGROUND OF THE INVENTION

Molecular chirality plays an important role in science and technology. The biological activities of many pharmaceuticals, fragrances, food additives and agrochemicals are often associated with their absolute molecular configuration. While one enantiomer gives a desired biological function through interactions with natural binding sites, another enantiomer usually does not have the same function and sometimes has deleterious side effects. A growing demand in pharmaceutical industries is to make chiral drugs in enantiomerically pure form. To meet this fascinating challenge, chemists have explored many approaches for acquiring enantiomerically pure compounds ranging from optical resolution and structural modification of naturally occurring chiral substances to asymmetric catalysis using synthetic chiral catalysts and enzymes. Among these methods, asymmetric catalysis is perhaps the most efficient because a small amount of a chiral catalyst can be used to produce a large quantity of a chiral target molecule. During the last several decades, great attention has been devoted to discovering new asymmetric catalysts and more than a half-dozen commercial industrial processes have used asymmetric catalysis as the key step in the production of enantiomerically pure compounds. The worldwide sales of chiral drugs in 1997 was nearly $90 billion.

Many chiral phosphines have been made to facilitate asymmetric reactions. Among these ligands, BINAP is one of the most frequently used bidentate chiral phosphines. The axiallay dissymmetric, fully aromatic BINAP ligand has been demonstrated to be highly effective for many asymmetric reactions. DUPHOS and related ligands have also shown impressive enantioselectivities in numerous reactions. However, these phosphines are difficult to make and some of them are air sensitive. Recently, chiral nitrogen ligands have been extensively studied for asymmetric reactions. Particularly, oxazolinyls derived from chiral amino alcohols are popular ligands. Recognition of secondary interaction between ligands and substrates have also been used to design asymmetric catalysts. For example, primary and secondary amines may form H-bonds with substrates.

SUMMARY OF THE INVENTION

An object of the present invention is the development of novel transition metal complexes with new families of amine oxazolinyl ligands for practical asymmetric synthesis. Several new families of chiral amine oxazolinyl ligands for asymmetric catalysis are embodied herein, including secondary amine oxazolinyl ligands, and amine oxazolinyl ligands having more than one oxazolinyl group.

A further object of the invention is the preparation of the chiral oxazolinyl from chiral amino alcohols.

A further object of the invention is the discovery of chiral tridentate and tetradentate ligands suitable for asymmetric catalysis. Particularly, these ligands have been demonstrated to be highly effective for Ru-catalyzed transfer hydrogenation of ketones and imines.

A further object of the invention is the improved catalysis of transition metal facilitated reactions such as hydrogenation, hydride transfer reaction, hydrosilylation, hydroboration, hydrovinylation, hydroformylation, hydrocarboxylation, allylic alkylation, cyclopropanation, Diels-Alder reaction, Aldol reaction, Heck reaction, Michael addition, and rearrangement reactions, leading to efficient and practical methods for producing important chiral drugs and agrochemicals.

To achieve the objects and in accordance with the purpose of the invention as embodied and broadly described herein, the invention comprises a chiral ligand that forms a catalyst providing enhanced enantiomeric selectivity in asymmetric reactions, having a structure selected from the group consisting of the enantiomers of the following formulas (I) through (IV):

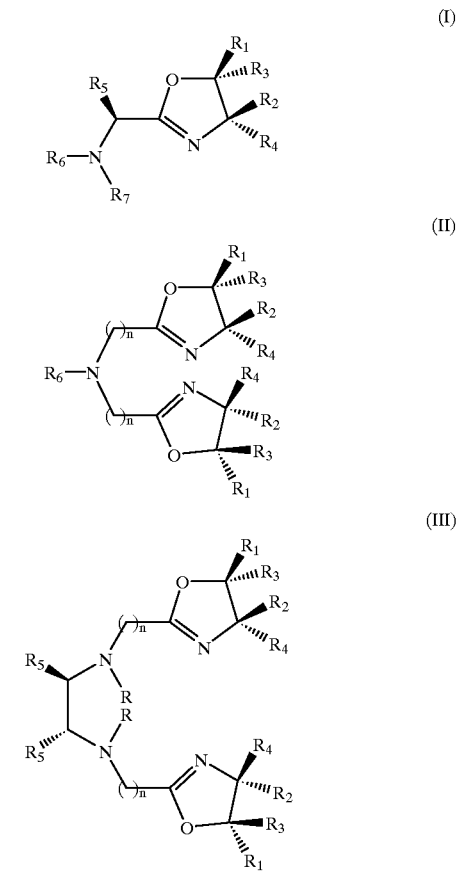

-continued

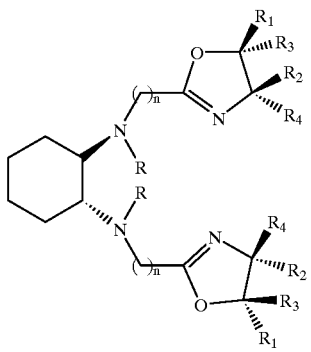

(IV)

wherein R, $R_1$, $R_2$, $R_3$, $R_4$, $R_5$, $R_6$ and $R_7$ are independently hydrogen, alkyl, aryl, substituted alkyl or substituted aryl, wherein any two of $R_1$, $R_2$, $R_3$ and $R_4$, may be linked to each other to form ring structures, wherein any two of $R_5$, $R_6$ and $R_7$ may be linked to each other to form a ring structure, and wherein n is 1 or 2.

DETAILED DESCRIPTION OF THE PREFERRED EMBODIMENTS

Asymmetric catalytic transfer hydrogenation using 2-propanol as a hydrogen source offers an attractive route for reducing unsymmetric ketones to chiral alcohols. Among the recently developed efficient transition-metal-based chiral catalysts, the most notable is the Ru(II)-TsDPEN (N-(p-tolylsulfonyl)-1,2-diphenylethylene-diamine) system reported by R. Noyori, et al., "Asymmetric Transfer Hydrogenation Catalyzed by Chiral Ruthenium Complexes," Acc. Chem. Res., Vol. 30, No. 2, pp. 97–102 (1997) and K. Haack, et al., "The Catalyst Precursor, Catalyst and Intermediate in the Ru$^{II}$-promoted Asymmetric Hydrogen Transfer Between Alcohols and Ketones," Angew. Chem. Int. Engl., Vol. 36, No. 3 pp. 285–288 (1997), which are incorporated herein in their entirety. They suggest that an NH moiety in the ligand may promote a cyclic transition state through hydrogen bonding to a ketone substrate, greatly increasing substrate affinity to the catalyst active site, inducing high activity and optical purity. Other reports have shown a similar "NH effect", for example, J. Gao, et al. "A Ruthenium(II) Complex with a $C_2$ symmetric Diphosphine/Diamine Tetradentate Ligand for Asymmetric Transfer Hydrogenation of Aromatic Ketones," Organometallics, Vol. 15, No. 4, pp. 1087–1089 (1996) and P. Gamez, et al., "Asymmetric Catalytic Reduction of Carbonyl Compounds Using $C_2$ symmetric Diamines as Chiral Ligands," Tetrahedron: Asymmetry, Vol. 6, No. 3, pp. 705–718 (1995), which are incorporated herein in their entirety.

In an effort to develop chiral tridentate ligands for asymmetric catalysis, we have designed the bis (oxazolinylmethyl)amine ("AMBOX") ligand system. Chiral tridentate ligands tend to form a deep chiral pocket around the metal center once coordinated to a transition metal. A good example is the well known PYBOX ligand family, disclosed, for example by H. Nishiyama, "Chiral and $C_2$-Symmetrical Bis(oxazolinylpyridine)rhodium(III) Complexes: Effective Catalysts for Asymmetric Hydrosilylation of Ketones," Organometallics, Vol. 8, No. 3, pp. 846–48 (March 1989). This catalyst has been successfully applied to the catalysis of asymmetric reactions. The two R groups on the oxazoline rings of PYBOX form a highly enantioselective "chiral fence," which enables better differentiation of the Re and Si faces of incoming substrates.

Figure 4:
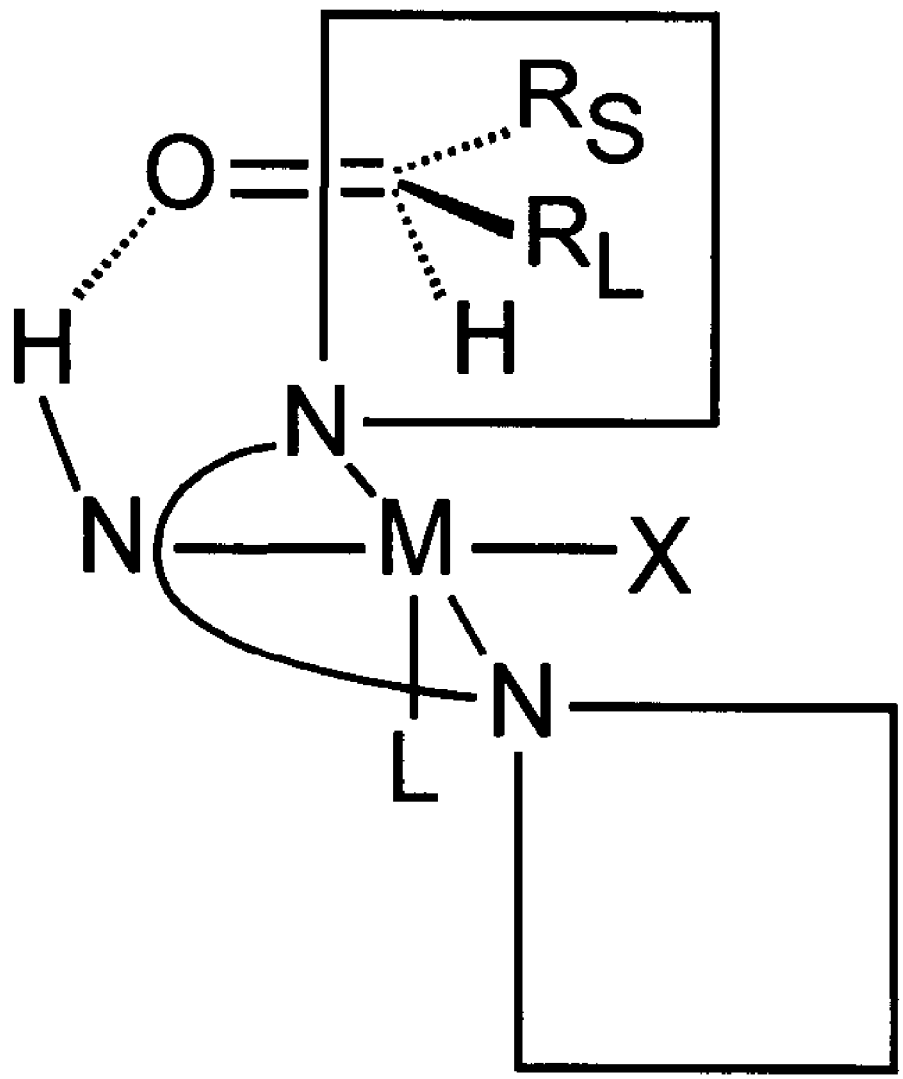
FIG. 4 is a schematic depiction of transition metal catalysts of chiral tridentate nitrogen ligands with an NH function, showing the cyclic transition state obtained in the transfer hydrogenation of prochiral ketones.

By replacing the pyridine backbone of PYBOX with an amine function, the new ligand AMBOX undergoes cyclic transition states similar to those suggested in the Noyori and Haack articles cited above and effectively catalyzes asymmetric transformations—for instance, the hydride-transfer reduction of ketones. FIG. 4 is a schematic depiction of the cyclic transition state obtained in the transfer hydrogenation of prochiral ketones.

Figure 1:
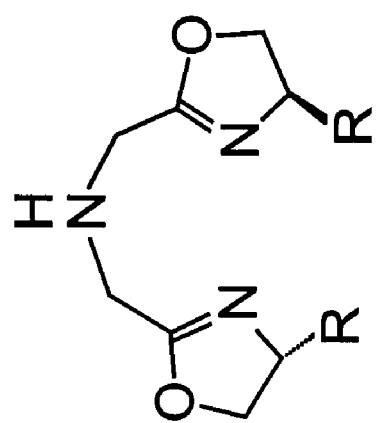
FIG. 1 shows a general synthesis route for a bis (oxazolinylmethyl)amine (hereinafter "AMBOX") ligand in a preferred embodiment of the present invention.
Figure 1:
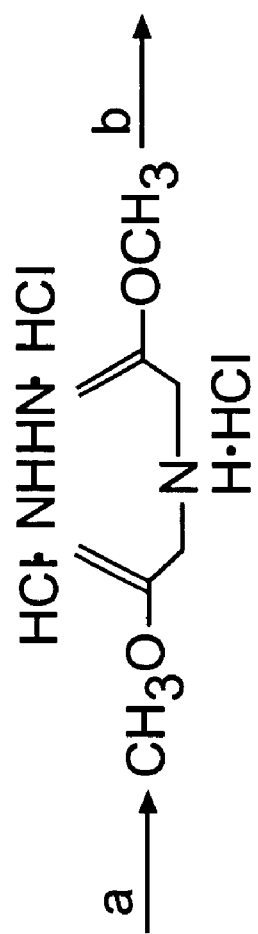
Figure 1:
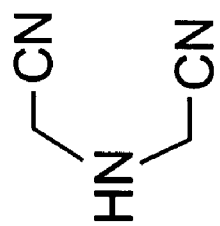

FIG. 1 depicts a preferred synthetic route for bis[4-(R)-phenyloxazolin-2-yl-methyl]amine (hereinafter "(R)—Ph-AMBOX"), a preferred embodiment of the present invention. A cyanoamine is reacted at a with HCl and methyl alcohol to form an imidate ester hydrochloride in 76% crude yield. The obtained imidate hydrochloride is reacted at b without further purification with an (R)-phenyl glycinol in dichloromethane at between 0° C. and room temperature for twelve hours. (R)—Ph-AMBOX was obtained in 15% yield.

The chirality of the oxazolinyl amine product as well as the identity of the substituents may be determined by choosing a different amino alcohol for step b. For example, to form preferred structure XI shown in FIG. 3, the amino alcohol

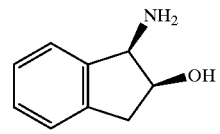

may be used in step b. In the scheme set forth in FIG. 1, the (S) amino alcohol may be used to achieve a product with opposite chirality.

The catalysts of the present invention are produced by complexing the herein described amine-oxazolinyl ligands with a transition metal. Suitable transition metal catalyst precursors for complexing with the chiral ligand of the present invention are known to those of ordinary skill in the art. For example, [Rh(cod)Cl]$_2$, [Rh(cod)$_2$]X, [Ir(cod)Cl]$_2$, [Ir(cod)$_2$]X, Ru(cod)Cl$_2$, where "cod" means 1,5-cyclooctadiene, and X stands for BF$_4$, ClO$_4$, SbF$_6$ CF$_3$SO$_3$, or equivalents, may be used. Alternatively, RuCl$_2$(PPh$_3$)$_3$, RuHCl(PPh$_3$)$_3$, RuX$_2$(PR$_3$)$_3$, RuHX(PR$_3$)$_3$, RuX$_2$, and other equivalents may be used, wherein X is halogen and R is a substituted or unsubstituted alkyl or aryl group.

Optimization of Catalyst

Initial test results on transfer hydrogenation of acetophenone in 2-propanol, using catalysts made in situ with AMBOX and various commonly used transition metal precursors were disappointing. Poor enantioselective performance prevailed among all these catalysts, with the highest enantiomeric excess (alternatively referred to as "ee" herein) of less than 50% obtained using RuCl$_2$(PPh$_3$)$_3$.

Table 1 presents the results of optimization of catalytic conditions for the transfer hydrogenation of acetophenone using (R)—Ph-AMBOX. Reaction (1) below was carried out in a 0.1 M acetophenone solution in 5 mL 2-propanol. The ratio of ketone: Ru$^{II}$: (R)—Ph-AMBOX was 100:1:1.1.

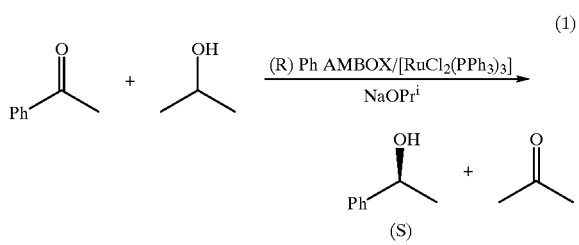

(1)

TABLE 1

| Entry | Free PPH$_3$[a] | NaOPr$^i$ equiv.[b] | T °C. | t h | yield[c] % | ee[c] % |
|---|---|---|---|---|---|---|
| 1[d] | + | 15 | 82 | 0.5 | 96 | 45 |
| 2[e] | + | 15 | 82 | .025 | 92 | 60 |
| 3 | + | 1.0 | 82 | 1 | 67 | 84 |
| 4 | − | 1.0 | 82 | 0.17 | 91 | 97 |
| 5 | − | 0.5 | 82 | 1 | 26 | 95 |
| 6 | − | 0 | 82 | 1 | 0 | N/A |
| 7 | − | 2.0 | 82 | 0.17 | 94 | 68 |
| 8 | − | 1.0 | 23 | 22 | 91 | 95 |

[a]"+" indicates free PPh$_3$ existed in the reaction mixture; "−" indicates that free PPh$_3$ was washed out with ether after the catalyst was formed, before adding acetphenone and NaOPr$^i$
[b]Equivalents of base to Ru$^{II}$
[c]% Yield and % enantiomeric excess were determined by GC analysis with a chiral Supelco β-DEX 120 capillary column. Absolute configurations were determined by comparing optical rotations with literature values. All major secondary alcohol products are (S) isomers.
[d]Catalyst made by stirring a mixture of R-(Ph)-AMBOX and RuCl$_2$(PPh$_3$)$_3$ at room temperature overnight.
[e]For entries 2–8, catalysts were prepared by refluxing R-(Ph)-AMBOX and RuCl$_2$(PPh$_3$)$_3$ at 82° C. for two hours.

It was found that an in situ catalyst made by refluxing AMBOX and RuCl$_2$(PPh$_3$)$_3$ in 2-propanol was far more effective than a catalyst made at room temperature. For entries 2 and 8 on Table 1, the catalysts were prepared by refluxing the RuCl$_2$(PPh$_3$)$_3$ precursor at 82° C. for two hours. These catalysts produced greater enantiomeric excess than the corresponding catalysts of entry 1, which were prepared overnight at room temperature. Thus, according to a preferred embodiment of the present invention, the catalysts are prepared by refluxing at the boiling temperature of 2-propanol.

Another factor that can drastically enhance both catalytic activity and enantioselectivity is the removal of free triphenylphosphine ligand released during the complexation of AMBOX before introducing acetophenone and base (NaOPr$^i$). Free PPh$_3$ may interfere with the reaction due to its ability to complex with the Ru center again. Removal of free PPh$_3$ reduces unfavorable competition to the enantioselective catalytic process. Preferably according to the invention, a mixture of RuCl$_2$(PPh$_3$)$_3$ precursor is heated with R—Ph-AMBOX for two hours, yielding a green solution. After the solvent is removed on vacuum, the resulting greenish residue is washed with ether to remove any free PPh$_3$. The solid is redissolved in 2-propanol, followed by addition of substrate and NaOPr$^i$. The enantiomeric excess increased dramatically from 84% to 97% upon such treatment, as may be seen by comparing entries 3 and 4 of Table 1.

Another important factor that can enhance activity and enantioselectivity is the molar ratio of NaOPr$^i$ to catalyst. This ratio should be about 1.0. When 0.5 molar equivalent of base was used, the reaction became very sluggish, although the enantiomeric excess remained high (entry 5, Table 1). When 2.0 molar equivalents of base were used, the reaction accelerated, but accompanied by severe erosion of enantiomeric excess (entry 7, Table 1).

FIG. 4 depicts the presumed active catalyst species conformation, wherein L represents PPh$_3$ and X represents chlorine. The species of FIG. 4 is probably formed after one HCl is extracted by one NaOPr$^i$ from the supposed precursor of RuCl$_2$PPh$_3$(AMBOX), followed by abstraction of one proton and one hydride from 2-propanol. The chloride across from the apical PPh$_3$ should be preferentially removed together with the NH proton, considering a strong trans effect from PPh$_3$. However, if more than one molar equivalent of base is introduced, the chloride across from NH could also be removed, resulting in possible pathways that favor the reverse reaction of ketone reduction, and hence a rapid loss of enantiomeric excess Free PPh$_3$ may also interfere with the reaction, due to its ability to complex with the ruthenium center again. Therefore, removal of free PPh$_3$ should see unfavorable competition to the enantioselective catalytic process diminished. Indeed, enantiomeric excess dramatically increased from 84% to 97% upon such treatment. (See entries 3–4 in Table 1).

Table 2 depicts the reduction of a variety of aromatic ketones to their secondary alcohols under optimized conditions using the catalyst of the present invention, with high enantiomeric excess and mostly satisfactory yield. The generic reaction (2) was carried out (except as otherwise stated) using a 0.1 M ketone solution in 5 mL 2-propanol. The ratio of ketone:Ru:(R)—Ph-Ambox:NaOPr$^i$ was 100:1:1.1:1.0.

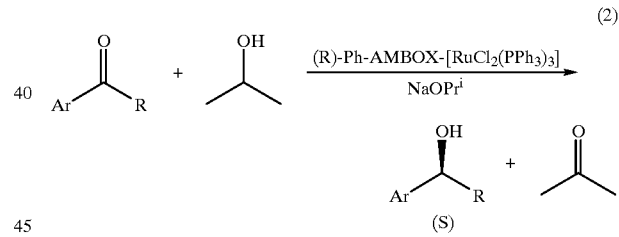

(2)

Various changes in substrates and catalytic reaction conditions are shown in Table 2 below.

TABLE 2

| Entry | Ketone | | t min | yield[a] % | ee[a] % |
|---|---|---|---|---|---|
| 1 | (phenyl ketone) | X = CH$_3$ | 5(10) | 80(91) | 98(97) |
| 2 | | X = Et | 10(20) | 77(92) | 95(92) |
| 3 | | X = i-Pr | 10 | 15 | 78 |
| 4 | (ortho-substituted phenyl ketone) | X = CH$_3$ | 40 | 96 | 98 |
| 5 | | X = Cl | 10 | 99 | 96 |
| 6 | | X = CH$_3$O | 4h | 3 | 19 |

TABLE 2-continued

| Entry | Ketone | | t min | yield[a] % | ee[a] % |
|---|---|---|---|---|---|
| 7 | 3-X-phenyl methyl ketone | X = CH$_3$ | 5(7) | 75(90) | 96(94) |
| 8 | | X = Cl | 10 | 5 | 92 |
| 9 | | X = CH$_3$O | 7(10) | 91(94) | 95(93) |
| 10 | 4-X-phenyl methyl ketone | X = CH$_3$ | 24h/rt | 61 | 96 |
| 11 | | X = Cl | 10 | 97 | 90 |
| 12 | | X = CH$_3$O | 10 | 41 | 98 |
| 13 | α-tetralone | | 10 | 42 | 95 |
| 14 | 1-acetonaphthone | | 2(5) | 72(98) | 96(94) |
| 14 | 2-acetonaphthone | | 2(7) | 55(91) | 96(92) | b. % Yield and % enantiomeric excess were determined by GC analysis with a chiral Supelco β-DEX 120 capillary column. Absolute configurations were determined by comparing optical rotations with literature values. All major secondary alcohol products are (S) isomers.

Both enantiomeric excess and chemical yield are delicately affected by substrates' steric and electronic properties. The steric hindrance effect of the alkyl sides of ketone substrates is apparent when comparing their results for methyl, ethyl and isopropyl phenyl ketones (entries 1 to 3, Table 2). By replacing the para substituent from chloride with a methoxy group, enantiomeric excess improved but with tremendous drop of conversion (entries 11, 12, Table 2). Erosion of product enantiomeric excess with increasing conversion is moderate for most of the ketones tested, especially for ortho methyl- and chloro-substituted acetophenones, which have barely seen any erosion at all throughout the reaction (entries 4, 5, Table 2). However, when phenyl ortho group is methoxy, very poor results were obtained (entry 6, Table 2).

Figure 2:
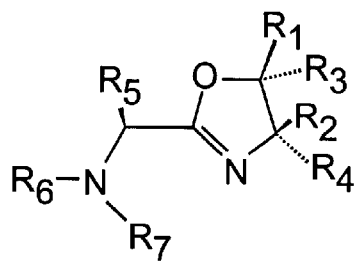
FIG. 2 shows the general structure of several chiral ligands according to preferred embodiments of the present invention.
Figure 2:
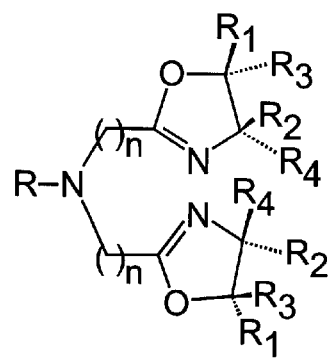
Figure 2:
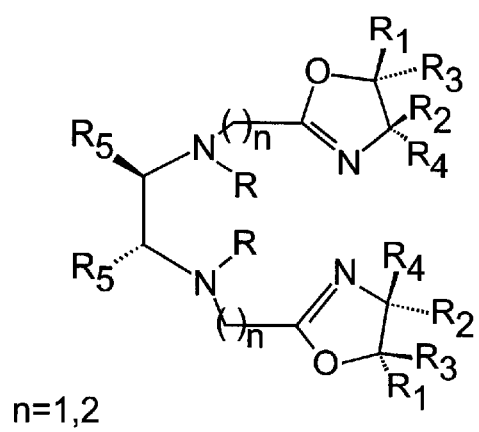
Figure 2:
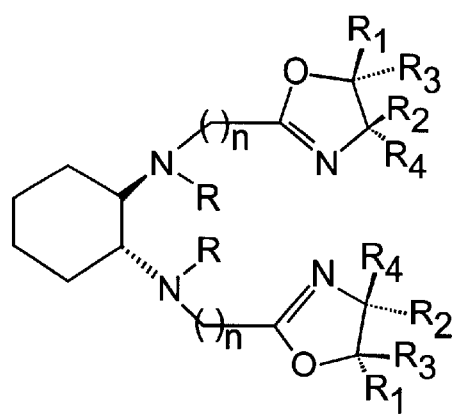

Formulas (I) to (IV) of FIG. 2 are non-limiting examples of preferred ligands in accordance with the present invention. As seen in FIG. 2, all of the preferred ligands according to the present invention comprise an oxazole substituted at the two position with an alkyl amine or substituted alkyl amine. As seen in Formula (I) for example, the alkyl amine substituted at the 2 position of the oxazole may be, for example, a methylamine or a substituted methylamine. Moreover, the amine may be a primary, secondary or tertiary amine as shown in FIG. 2.

In FIG. 2 R, R$_1$, R$_2$, R$_3$, R$_4$, R$_5$, R$_6$ and R$_7$ may the same or different and may be hydrogen, alkyl, aryl, substituted alkyl, or substituted aryl. Also within the scope of the invention are embodiments wherein any two of R$_1$, R$_2$, R$_3$ and R$_4$ may be linked to form a ring structure, and wherein any two of R$_5$, R$_6$ and R$_7$ may be linked to form a ring structure. For example, in Formula (II), where R$_1$ and R$_3$ are methyl and R$_2$ and R$_4$ are phenyl, a structure having the configuration of Formula (XI) is formed. Likewise, one of ordinary skill in the art would recognize many ring structures made possible by joining R$_1$ through R$_4$ in Formulas (I) through (IV). Alternatively, a ring formed by linking R$_5$ and R$_6$ could form a structure like that shown in Formula (VI).

Although only certain enantiomeric configurations are shown in the Figures, the enantiomeric orientation of the ligands may be manipulated using different reagents during synthesis. The enantiomers of the represented formulas are also within the scope of the invention.

Figure 3:
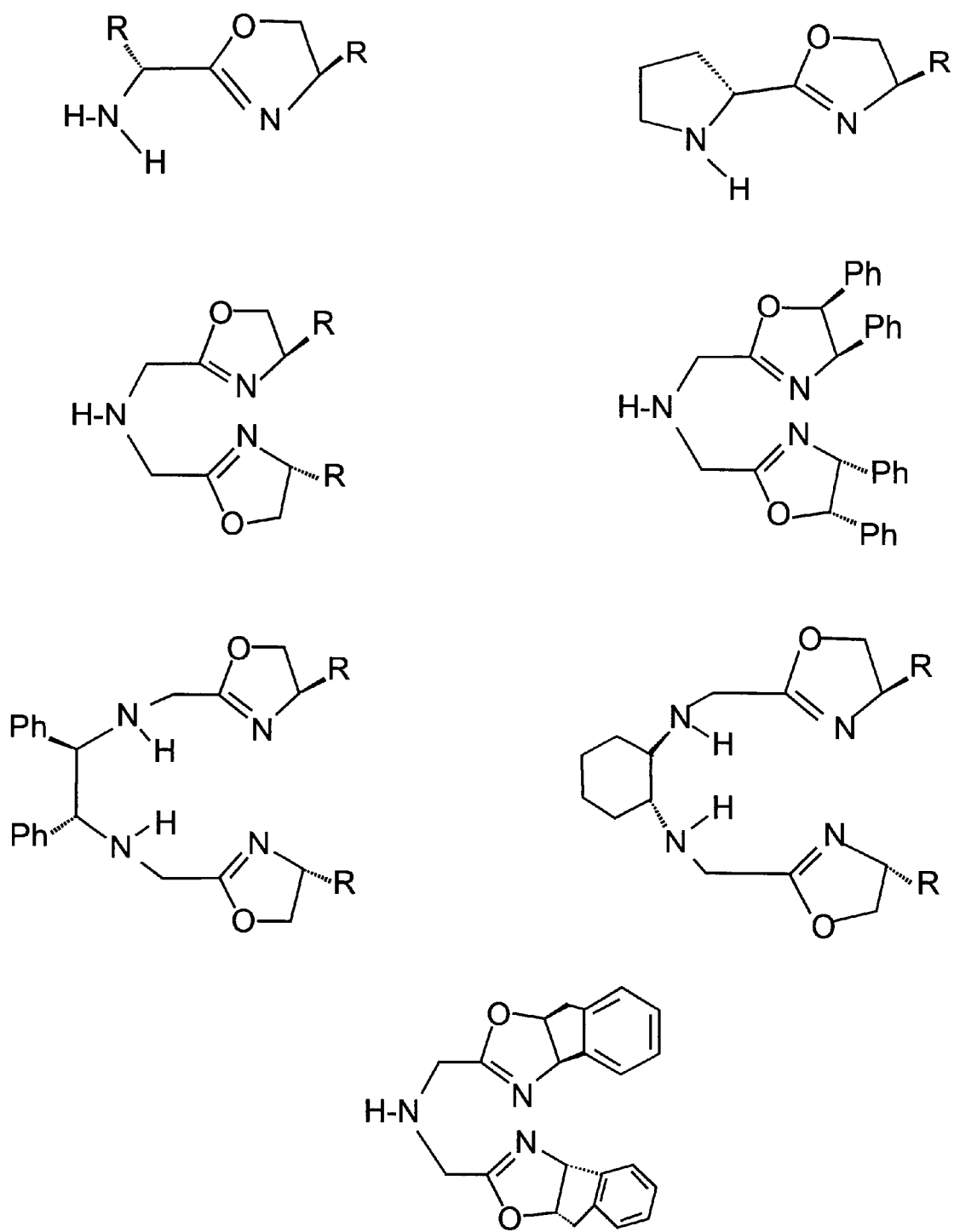
FIG. 3 shows specific examples of the chiral ligands according to preferred embodiments of the present invention.

FIGS. (V) through (XI) of FIG. 3 denote particularly preferred embodiments of the chiral amine oxazolinyl ligands of the present invention, such as, oxazolin-2-yl-methylamine, which may be substituted on the oxazole or the methyl as shown in Formula (V), or 2-oxazolin-2-yl-azacyclopentane which may be substituted on the oxazole as shown in Formula (VI), or the previously described bis[4-(R)-phenyloxazolin-2-yl-methyl]amine, which may be derived from Formula (VII).

In summary, this invention includes new chiral tridentate ligands which form a highly efficient catalyst with RuCl$_2$ (PPh$_3$)$_3$ and other catalyst precursors for transfer hydrogenation of a range of ketones and other reactions.

I claim:

1. A compound chosen from the enantiomers of formula (I), (II), (III), and (IV):

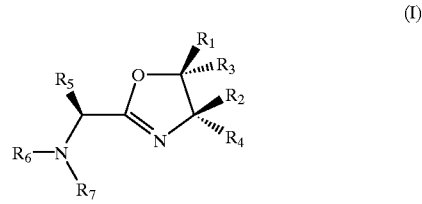

(I)

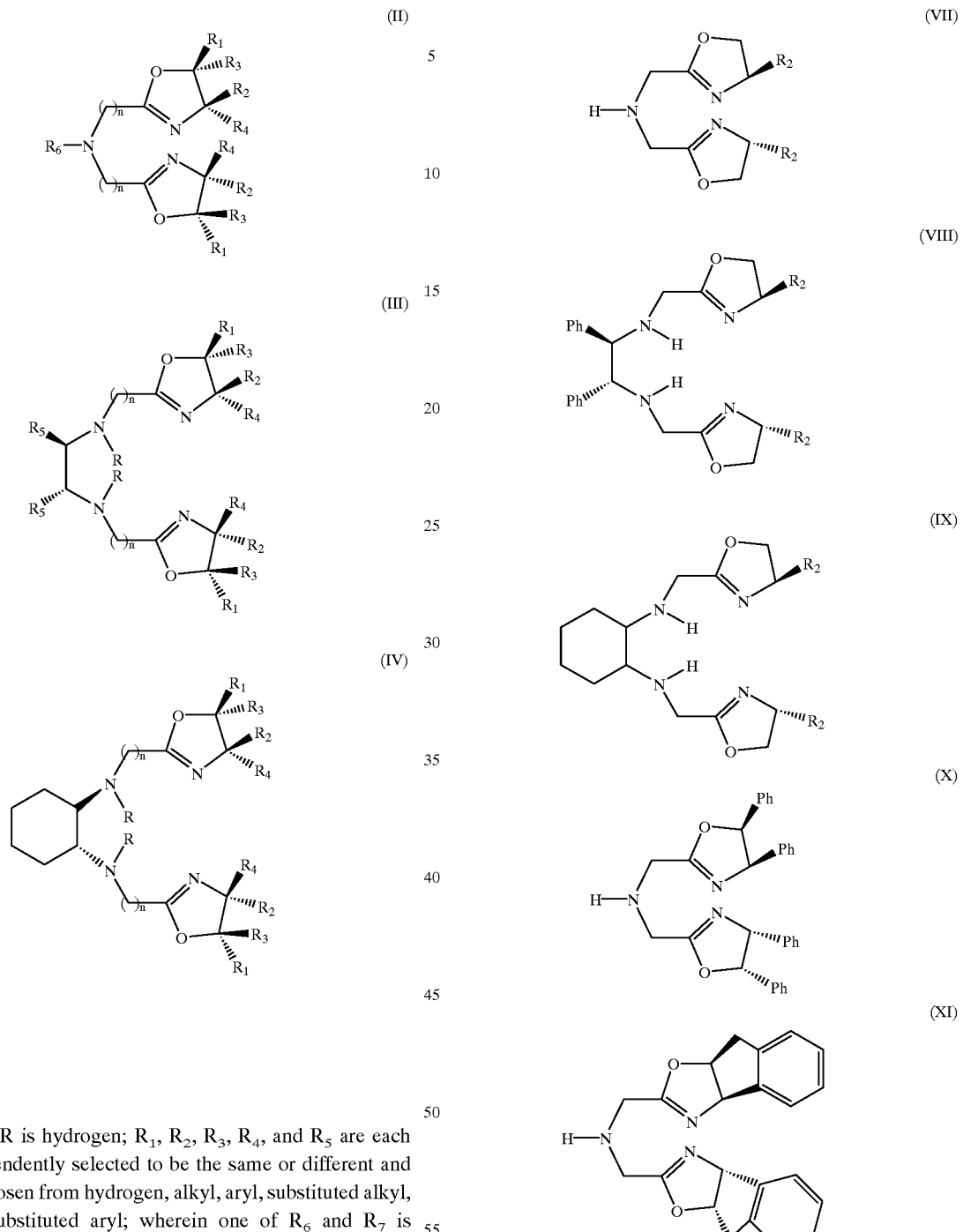

wherein R is hydrogen; $R_1$, $R_2$, $R_3$, $R_4$, and $R_5$ are each independently selected to be the same or different and are chosen from hydrogen, alkyl, aryl, substituted alkyl, and substituted aryl; wherein one of $R_6$ and $R_7$ is hydrogen and the other is chosen from hydrogen, alkyl, aryl, substituted alkyl, and substituted aryl;

wherein any two of $R_1$, $R_2$, $R_3$ and $R_4$ when linked together form a ring; wherein $R_5$, $R_6$ or $R_7$ when linked together form a ring, and n is 1 or 2; with the proviso that in formula (II), no more than three of $R_1$, $R_2$, $R_3$, or $R_4$ are the same.

2. A compound according to claim 1, wherein said compound is selected from formulas VII, VIII, IX, X, and (XI):

3. A compound according to claim 1, wherein said compound is a bis(oxazolinyl)amine.

4. A compound according to claim 7, wherein said bis(oxazolinyl)amine is bis[4-(R)-phenyloxazolin-2-yl-methyl]amine.

5. A process for making a compound according to claim 1, comprising reacting imidate ester with a chiral alcohol to form said compound of claim 1.

* * * * *

UNITED STATES PATENT AND TRADEMARK OFFICE
CERTIFICATE OF CORRECTION

PATENT NO. : 6,255,493 B1
DATED : July 3, 2001
INVENTOR(S) : Xumu Zhang

Page 1 of 1

It is certified that error appears in the above-identified patent and that said Letters Patent is hereby corrected as shown below:

<u>Column 9, claim 1,</u>
In the structure for formula (II), change "R6" to -- R --.

<u>Column 10, claim 4,</u>
Line 60, change "claim 7" to -- claim 3 --.

Signed and Sealed this

Twelfth Day of March, 2002

Attest:

JAMES E. ROGAN
*Attesting Officer*    *Director of the United States Patent and Trademark Office*